(12) United States Patent
Ishii et al.

(10) Patent No.: US 9,841,413 B2
(45) Date of Patent: Dec. 12, 2017

(54) DATA PROCESSING DEVICE AND AUTOMATIC ANALYSIS DEVICE USING SAME

(71) Applicant: Hitachi High-Technologies Corporation, Tokyo (JP)

(72) Inventors: Naomi Ishii, Tokyo (JP); Kumiko Kamihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 351 days.

(21) Appl. No.: 14/417,841

(22) PCT Filed: Jul. 3, 2013

(86) PCT No.: PCT/JP2013/068276
§ 371 (c)(1),
(2) Date: Jan. 28, 2015

(87) PCT Pub. No.: WO2014/021047
PCT Pub. Date: Feb. 6, 2014

(65) Prior Publication Data
US 2015/0198579 A1    Jul. 16, 2015

(30) Foreign Application Priority Data

Jul. 30, 2012  (JP) ................................ 2012-168818

(51) Int. Cl.
| | |
|---|---|
| *G01N 33/483* | (2006.01) |
| *G01N 35/00* | (2006.01) |
| *G01N 1/00* | (2006.01) |

(52) U.S. Cl.
CPC ............. *G01N 33/483* (2013.01); *G01N 1/00* (2013.01); *G01N 35/00603* (2013.01); *G01N 2001/002* (2013.01); *G01N 2035/00673* (2013.01)

(58) Field of Classification Search
None
See application file for complete search history.

(56) References Cited

U.S. PATENT DOCUMENTS

| | | | |
|---|---|---|---|
| 5,067,092 A | 11/1991 | Hamann | |
| 2005/0175503 A1* | 8/2005 | Shiba | ............... G01N 35/00663 422/64 |

(Continued)

FOREIGN PATENT DOCUMENTS

| | | |
|---|---|---|
| JP | 07-120471 | 5/1995 |
| JP | 2009-204448 | 9/2009 |

(Continued)

OTHER PUBLICATIONS

International Preliminary Report on Patentability for International Application No. PCT/JP2013/068276 dated Feb. 12, 2015.

(Continued)

*Primary Examiner* — Mischita Henson
(74) *Attorney, Agent, or Firm* — Mattingly & Malur, PC

(57) ABSTRACT

An automatic analysis device includes: a factor storage unit 12b which stores each factor previously specified as a factor that could affect measurement accuracy of each of measurement items, while associating each factor with each measurement item; an abnormality judgment unit 103a which judges the presence/absence of an abnormality in a measurement value of each measurement item on the basis of an approximation formula and approximation formula parameters stored in an approximation formula storage unit 12a; and a factor judgment unit 103b which refers to the results of the judgment by the abnormality judgment unit 103a in a preset order, and would judge as an abnormality factor a factor stored in the factor storage unit 12b in association with a measurement item as an abnormality factor in a case where a plurality of measurement values regarding the measurement item have consecutively been judged to be abnormal. The operator is informed of the abnormality factor on the basis of the result of the judgment by the factor judgment unit 103b. With this configuration, deterioration in the measurement accuracy can be reduced through the (Continued)

detection of an abnormality in the measurement result and the determination of the causative factor.

3 Claims, 5 Drawing Sheets

(56) References Cited

U.S. PATENT DOCUMENTS

2009/0222213 A1 9/2009 Hamazumi et al.
2012/0064636 A1 3/2012 Mitsuyama et al.

FOREIGN PATENT DOCUMENTS

JP 2010-271095 12/2010
JP EP 2434292 A1 * 3/2012 ....... G01N 35/00623

OTHER PUBLICATIONS

Chinese Office Action received in corresponding Chinese Application No. 201380040431.4 dated Aug. 21, 2015.
Chinese Office Action received in corresponding Chinese Application No. 201380040431.4 dated Feb. 1, 2016.
Extended European Search Report received in corresponding European Application No. 13825801.7 dated Feb. 19, 2016.
Japanese Office Action received in corresponding Japanese Application No. 2012-168818 dated Apr. 5, 2016.

* cited by examiner

FIG. 4

SETTING (400)

| KEY INFORMATION (401) | k | A1 | A0 (402) | Err | p | q | D0 | T1 |
|---|---|---|---|---|---|---|---|---|
| CELL ▽ | 5 | 3 | 6 | 2 | – | – | – | – |
| STIRRING MECHANISM ▽ | – | 3 | 6 | 3 | – | – | – | – |
| REAGENT ▽ | – | 3 | 6 | 3 | – | – | – | – |

OK (403)  CANCEL (404)

FIG. 5

ALL DATA (500)

LINE SORTING : ANALYSIS DEVICE ☑FIRST ☐SECOND ☐THIRD ☐FOURTH (503)

SAMPLE ID ▽ (501)   ITEM ▽ (502)   COLUMN DISPLAY NUMBER : 33 ▽ (504)

START (505)

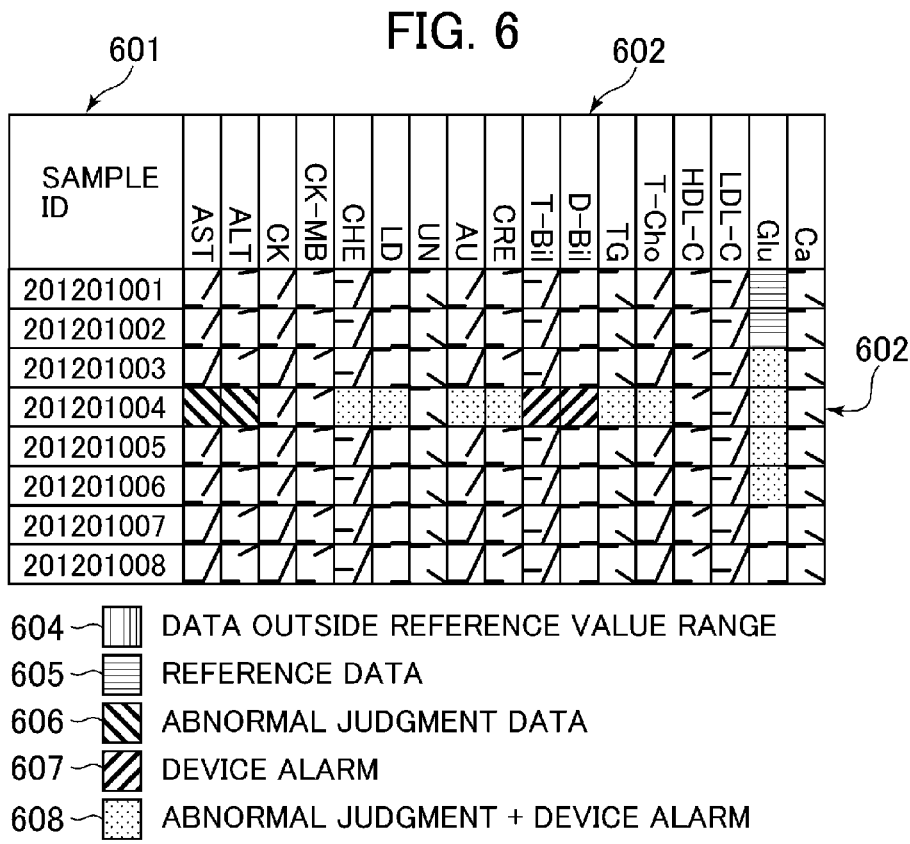
FIG. 6
- 604 — DATA OUTSIDE REFERENCE VALUE RANGE
- 605 — REFERENCE DATA
- 606 — ABNORMAL JUDGMENT DATA
- 607 — DEVICE ALARM
- 608 — ABNORMAL JUDGMENT + DEVICE ALARM
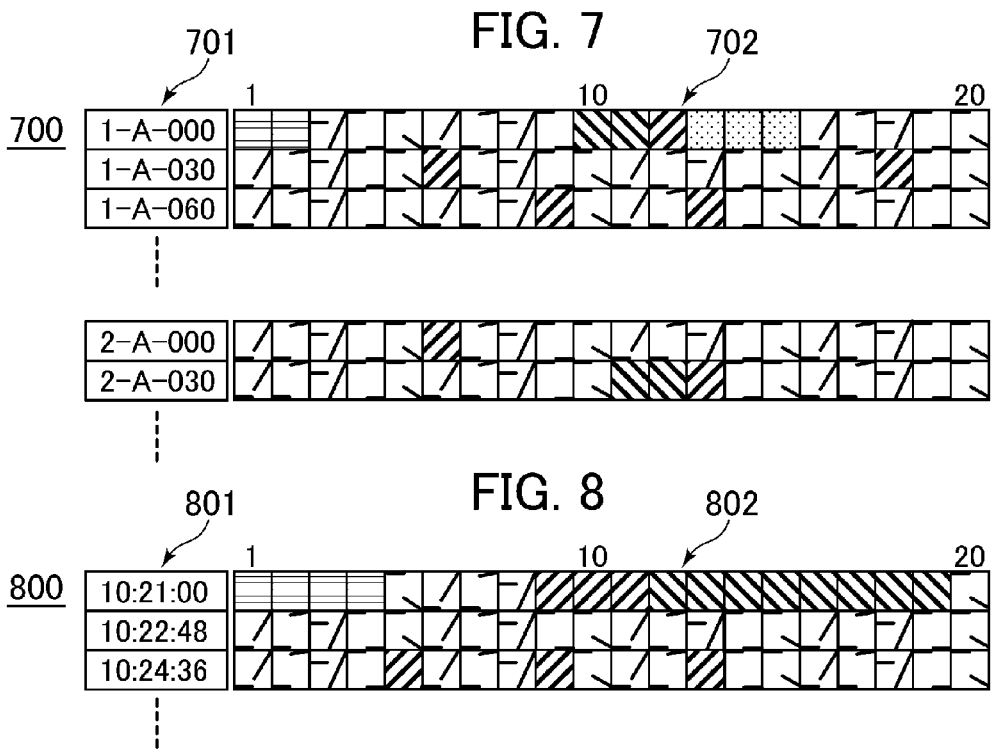
FIG. 7
FIG. 8

| KEY INFORMATION | SCORE | ANALYSIS RESULT COMMENT |
|---|---|---|
| UNIT 1, CELL 16 | 5 | A0 DEVIATION OCCURRED CONSECUTIVELY |
| UNIT 1, STIRRING MECHANISM 1 | 5 | T1 DEVIATION OCCURRED CONSECUTIVELY |
| UNIT 1, AST | 10 | q DEVIATION OCCURRED CONSECUTIVELY |

DATA PROCESSING DEVICE AND AUTOMATIC ANALYSIS DEVICE USING SAME

TECHNICAL FIELD

The present invention relates to a data processing device for processing data acquired in measurement of a sample, and to an automatic analysis device where the data processing device is employed.

BACKGROUND ART

In an automatic analysis device for clinical examination, for example, a characteristic value, including concentration and activity value, of a substance to be measured in a biological sample such as blood or urine (hereinafter referred to as a "sample") is determined by mixing a certain amount of the biological sample with a certain amount of a reagent, stirring the mixture (reaction solution) to make the sample and the reagent react with each other, and measuring time-variation of the absorbance of the reaction solution. Deterioration in the measurement accuracy is reduced by grasping the status of the automatic analysis device or the sample by performing measurement of a standard solution for calibrating the reagent, a quality control sample for checking the status of the analysis device or the reagent for each analysis item.

As an example of such an automatic analysis device, Patent Literature 1 (JP-2009-204448-A) discloses technology regarding an automatic analysis device that determines a reaction rate constant from the time-variation of the absorbance stored as data along the time line by using an approximation formula and judges if the reaction is abnormal on the basis of the value of the reaction rate constant.

PRIOR ART LITERATURE

Patent Literature

Patent Literature 1: JP-2009-204448-A

SUMMARY OF THE INVENTION

Problem to be Solved by the Invention

The measurement accuracy of an automatic analysis device is determined by a combination of a plurality of performance control factors such as the dispensation quantity (dispensation accuracy) of the sample or the reagent to the reaction cell and the uniformity/stability of the reagent or the standard solution. Thus, in a case where an abnormality has occurred in a result of measurement, it would be necessary to eliminate the abnormality in the measurement result and reduce the deterioration in the measurement accuracy by determining the factor causing the abnormality (causative factor) and improving the status of the factor.

However, the aforementioned conventional technology has no description in regard to the determination of the causative factor even though the occurrence of an abnormality in the measurement result can be determined with the technology. Specifically, in a case where an abnormality has occurred in an automatic analysis device for clinical examination, it will be extremely difficult for the operator to quickly determine the causative factor in regard to a large number of samples to be analyzed and improve the situation. The conventional technology has plenty of room for improvement in this regard.

An object of the present invention, which has been made in consideration of the above-described situation, is to provide a data processing device capable of reducing the deterioration in the measurement accuracy by detecting an abnormality in the measurement result and determining the causative factor, and to provide an automatic analysis device where such a data processing device is employed.

Means for Solving the Problem

To achieve the above object, a data processing device according to the present invention includes: an approximation formula storage unit which stores an approximation formula of time-variation of a measurement value regarding each of measurement items and parameters specifying the approximation formula in regard to each measurement item; a factor storage unit which stores each factor previously specified as a factor that could affect measurement accuracy of each of the measurement items, while associating each factor with each measurement item; an abnormality judgment unit which judges the presence/absence of an abnormality in the measurement value of each measurement item on the basis of the approximation formula and the parameters of the approximation formula; a factor judgment unit which refers to the results of the judgment by the abnormality judgment unit in a preset order of measurement objects, and would judge as an abnormality factor a factor stored in the factor storage unit in association with a measurement item in a case where a plurality of measurement values regarding the measurement item have consecutively been judged to be abnormal; and a notification unit which notifies an operator of the abnormality factor on the basis of the result of the judgment by the factor judgment unit.

Effect of the Invention

According to the present invention, the deterioration in the measurement accuracy can be reduced through the detection of an abnormality in the measurement result and the determination of the causative factor.

BRIEF DESCRIPTION OF THE DRAWINGS

FIG. 4 is a schematic diagram showing an approximation parameter

FIG. 5 is a schematic diagram showing a rough design of a data reference screen for setting display conditions of measurement result on a measurement result display screen.

FIG. 6 is a schematic diagram showing an example of a measurement result display screen which is displayed on a display unit when a sample unit has been judged as an abnormality factor.

FIG. 7 is a schematic diagram showing an example of a measurement result display screen which is displayed on the display unit when a reagent pipetter has been judged as an abnormality factor.

FIG. 8 is a schematic diagram showing an example of a measurement result display screen which is displayed on the display unit when a reaction cell unit has been judged as an abnormality factor.

MODE FOR CARRYING OUT THE INVENTION

With reference to the drawings, a description will be given in detail of a preferred embodiment of the present invention.

Figure 1:
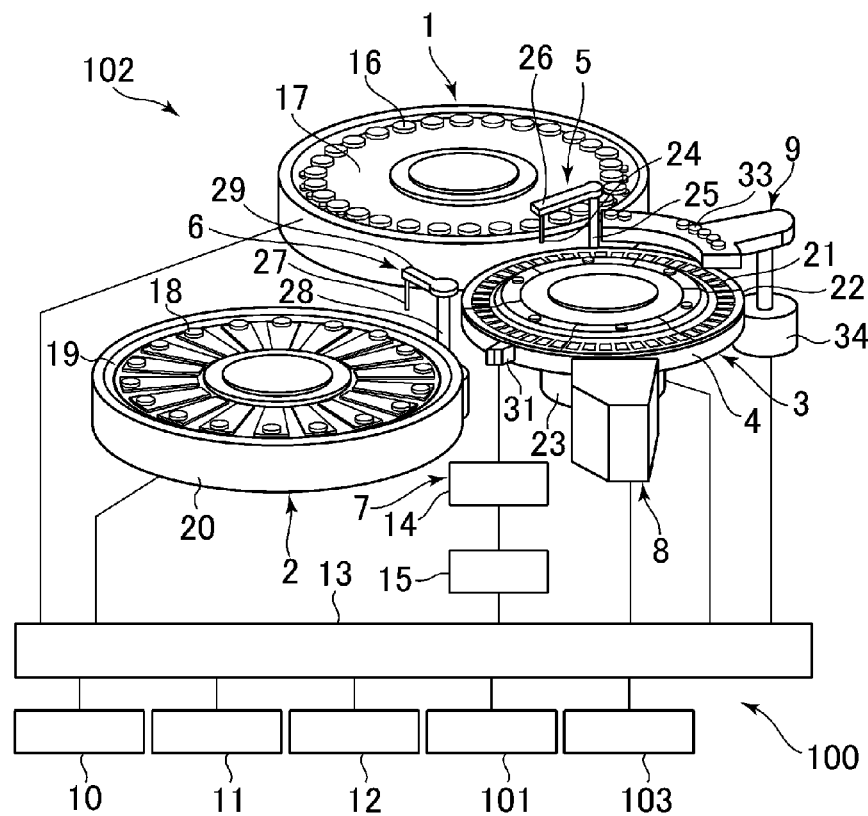
FIG. 1 is a schematic diagram showing the overall configuration of an automatic analysis device including a data processing device according to an embodiment of the present invention.
Figure 2:
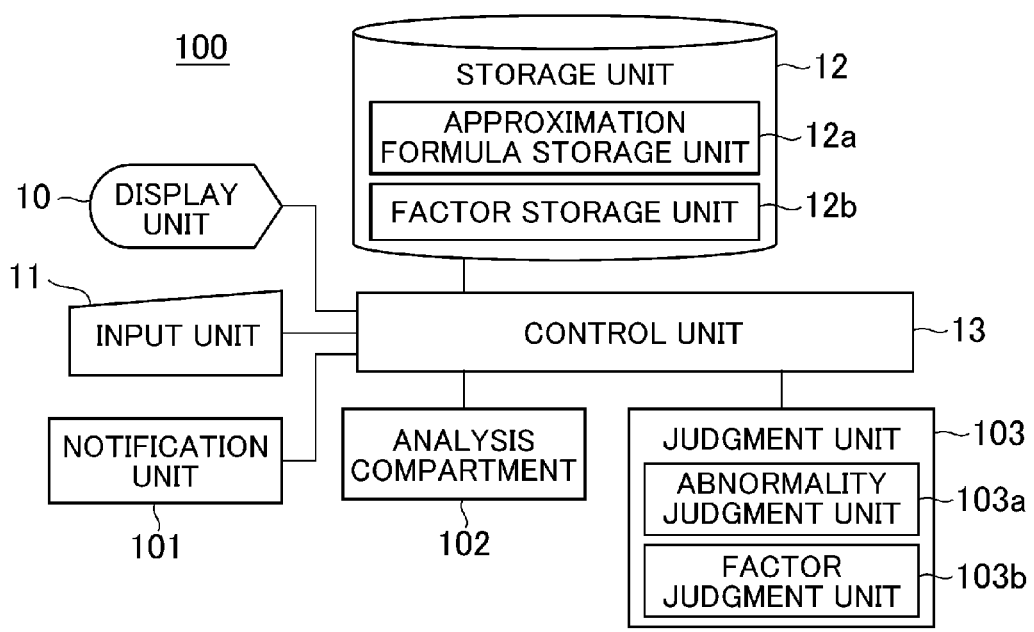
FIG. 2 is a block diagram showing the details of the automatic analysis device of the embodiment together with an analysis compartment.

FIG. 1 is a schematic diagram showing the overall configuration of an automatic analysis device including a data processing device according to an embodiment of the present invention. FIG. 2 is a block diagram showing the details of the automatic analysis device together with an analysis compartment.

With reference to FIG. 1, the automatic analysis device includes: an analysis compartment 102 for performing a variety of processing and measurement on samples; and a control unit 100 for controlling the operation of components of the analysis compartment 102 and the operation of the entire automatic analysis device and for processing information supplied from the analysis compartment 102.

The analysis compartment 102 mainly includes a sample disk 1, a reagent disk 2, a reaction disk 3, a sample pipetter 5, a reagent pipetter 6, a stirring mechanism 7, a photometry mechanism (measurement unit) 8, a cleaning mechanism 9, and a controller 100. The sample disk 1 has a rotatable circular disk 17 on which sample bottles 16 storing samples are arranged circumferentially. The reagent disk 2 has a rotatable circular disk 19 on which reagent bottles 18 storing reagents are arranged circumferentially. The circular disk 19 is arranged in a cooling unit 20. The reaction disk 3 has a reaction cell holder 22 on which reaction cells 21, each used for reaction of a sample and a reagent mixed together, are arranged circumferentially. The reaction cell holder 22 can be rotated by a drive mechanism 23. The reaction cell holder 22 is arranged in a reaction bath 4. The sample pipetter 5 dispenses a sample stored in a sample bottle 16 into a reaction cell 21 by use of a probe 27 which is arranged at the tip end of an arm 29 rotatably supported by a support shaft 28. The reagent pipetter 6 dispenses a reagent stored in a reagent bottle 18 into the reaction cell 21 by use of a probe 24 which is arranged at the tip end of an arm 26 rotatably supported by a support shaft 25. The stirring mechanism 7 has a stirrer 31 for stirring the liquid mixture (reaction solution) of the sample and the reagent in the reaction cell 21 by means of vibration in accordance with a signal input from a piezoelectric element driver 14 controlled by a stirring mechanism controller 15. The photometry mechanism (measurement unit) 8 measures the absorbance of the reaction solution in the reaction cell 21. The cleaning mechanism 9 cleans the reaction cell 21 after the measurement with a cleaning liquid discharged from a nozzle 33 which can be driven vertically by a vertical drive mechanism 34. The controller 100 controls the operation of the entire automatic analysis device.

With reference to FIG. 2, the controller 100 includes a display unit 10, an input unit 11, a storage unit 12, a judgment unit 103, a notification unit 101, and a control unit 13. The display unit 10 displays setting screens (for making settings of setting information to be used for the measurement of samples) and measurement results. The input unit 11 is used for inputting a measurement command and setting information. The storage unit 12 stores the setting information, the measurement results, and programs used for the measurement. The judgment unit 103 makes a judgment on the presence/absence of an abnormality in a measurement value in an abnormality judgment process and makes a judgment on an abnormality factor in a factor judgment process. The notification unit 101 notifies the operator of a variety of information by use of sound and light. The control unit 13 is connected to the analysis compartment 102 and controls the operation of the entire automatic analysis device by controlling the controller 100, including the display unit 10, the input unit 11 and the storage unit 12, and the analysis compartment 102.

The storage unit 12 has a function of storing the setting information, the measurement results, the programs used for the measurement, analysis parameters, the analyzable number of times of each reagent bottle, the maximum analyzable number of times, and calibration results. Further, the storage unit 12 includes an approximation formula storage unit 12a having a function of storing an approximation formula of the time-variation of a measurement value regarding each of measurement items for a sample and parameters specifying the approximation formula in regard to each measurement item, and a factor storage unit 12b having a function of storing each factor previously specified as a factor that could affect the measurement accuracy of each measurement item while associating each factor with each measurement item.

The automatic analysis device needs to use an analysis device, a reagent for each analysis item, a standard solution for calibrating each reagent, and a quality control sample for measurement for checking the status of each reagent. The final analytical performance of the automatic analysis device is determined in accordance with the combination of the status and accuracy of these elements. Factors inside the analysis device directly influencing the analytical performance include a sample pipetter, the reagent pipetter, the stirring mechanism, an optical system, the reaction cells, and a constant temperature bath, for example. Factors other than those inside the automatic analysis device include the quality and ingredients of the samples, the reagents, the standard solutions and the quality control samples, for example.

The judgment unit 103 includes an abnormality judgment unit 103a and a factor judgment unit 103b. The abnormality judgment unit 103a makes the judgment on the presence/absence of an abnormality in the measurement value of each measurement item on the basis of the approximation formula and the approximation formula parameters stored in the approximation formula storage unit 12a. The factor judgment unit 103b refers to the results of the judgment by the abnormality judgment unit 103a in a preset order of measurement objects, and would judge as an abnormality factor a factor stored in the factor storage unit 12b in association with a measurement item in a case where a plurality of measurement values regarding the measurement item have consecutively been judged to be abnormal.

In the automatic analysis device configured as above, the analytical process is performed as follows: First, the rotation of the circular disk 17 of the sample disk 1 is controlled by the control unit 13, each sample bottle 16 storing a sample to be measured is transferred to a sample dispensation position for the sample pipetter 5 in accordance with the order of samples to be analyzed, and the sample in the sample bottle 16 is dispensed by the sample pipetter 5 into a reaction cell 21 which has been transferred to the sample dispensation position. Subsequently, the rotation of the circular disk 19 is controlled, a reagent bottle 18 storing a reagent to be dispensed into the sample to be analyzed is transferred to a reagent dispensation position for the reagent pipetter 6, and the reagent in the reagent bottle 18 is dispensed by the reagent pipetter 6 into the reaction cell 21 which has been transferred to the reagent dispensation position. Then, the reaction cell 21 is transferred to the stirring mechanism 7 and undergoes the stirring by the stirring mechanism 7. Thereafter, the dispensation of a reagent (another reagent) at the reagent dispensation position and the stirring are performed alternately.

The liquid mixture of the sample and the reagent dispensed into the reaction cell 21 and stirred (reaction solution) undergoes measurement by the photometry mechanism (measurement unit) 8. The photometry mechanism 8 measures the absorbance of the reaction solution on the basis of the transmission of a light beam from a light source through the reaction solution. The measurement result (absorbance) is stored in the storage unit 12 via the control unit 13. Further, the measurement result is converted by the control unit 13 into concentration information on the sample to be measured, stored in the storage unit 12, and displayed on the display unit 10 as the measurement result. Furthermore, the control unit 13 performs the abnormality judgment process and the factor judgment process based on the absorbance of the reaction solution. The reaction cell 21 after the measurement is transferred to the position of the cleaning mechanism 9 (cleaning position), undergoes the cleaning process, and is used for a subsequent analysis.

Figure 3:
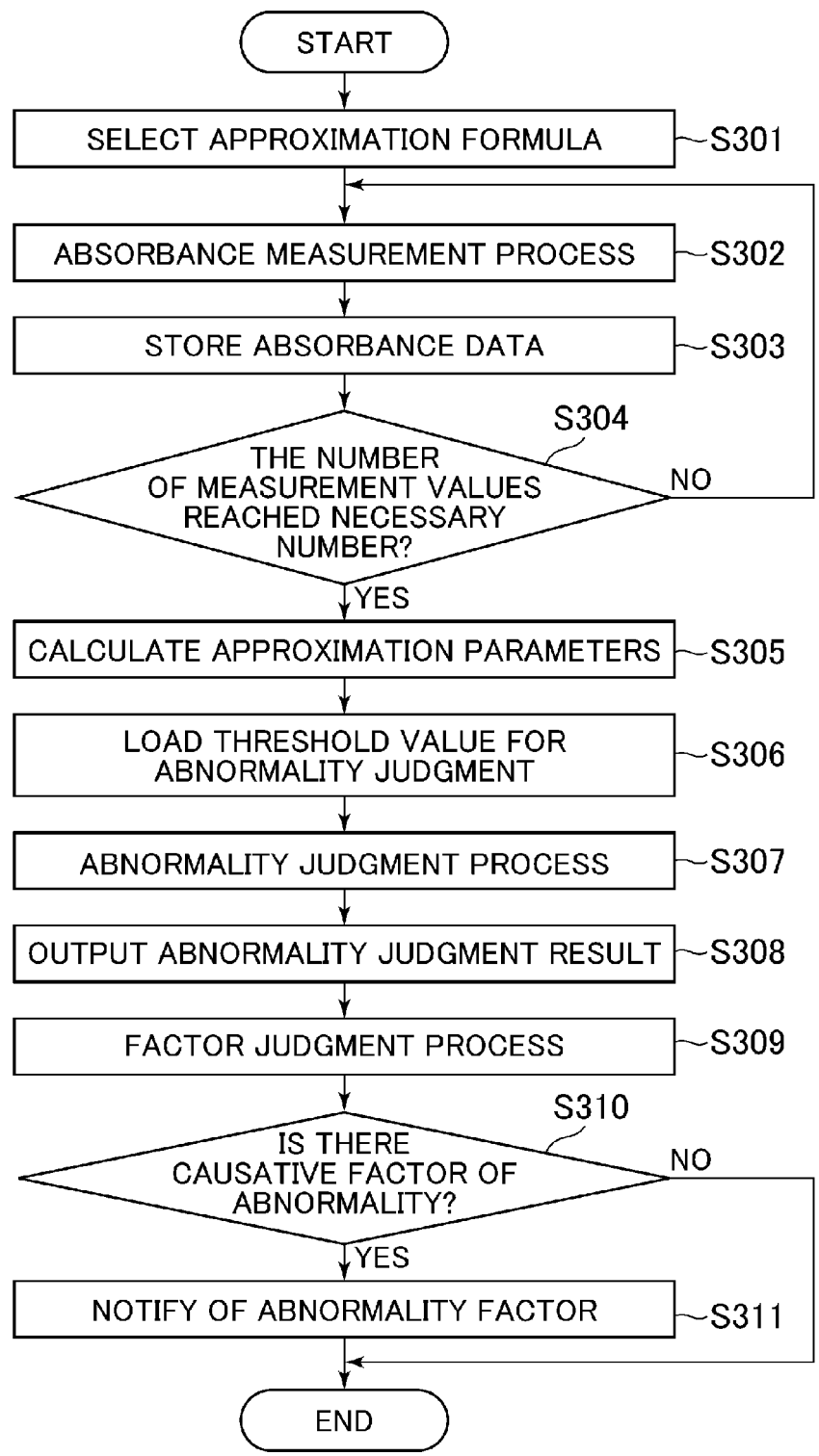
FIG. 3 is a flow chart showing an analytical process.

FIG. 3 is a flow chart showing the analytical process performed by the automatic analysis device according to the present embodiment.

As shown in FIG. 3, when the start of the analysis is commanded through the input unit 11 or the like, the control unit 13 of the controller 100 first selects the approximation formula stored corresponding to the measurement item and reads out the selected approximation formula from the approximation formula storage unit 12a of the storage unit 12 (step S301). Subsequently, the control unit 13 performs an absorbance measurement process (for measuring the absorbance in the analytical process of the sample to be measured in the analysis compartment 102 (step S302) and stores the absorbance measurement result in the storage unit 12 (step S303). Subsequently, the control unit 13 judges whether a necessary number of absorbance measurement values for calculating the approximation parameters from the approximation formula have been acquired (step S304). If the result of the judgment is negative, the control unit 13 repeats the steps S302 and S303 until the number of the measurement values reaches the necessary number and the judgment in the step S304 becomes affirmative. If the result of the judgment in the step S304 is affirmative, the control unit 13 calculates the parameters specifying the approximation formula (approximation parameters) from the measurement results and stores the calculated approximation parameters in the approximation formula storage unit 12a (step S305).

Subsequently, the control unit 13 reads out a threshold value to be used for the abnormality judgment process from the storage unit 12 (step S306), performs the abnormality judgment process of judging that an abnormality has occurred in a measurement value if an approximation parameter exceeds the threshold value read out from the storage unit 12 (step S307), and outputs the result of the abnormality judgment to the storage unit 12 and the display unit 10 (step S308).

Subsequently, the control unit 13 performs the factor judgment process of referring to the results of the judgment of the abnormality judgment process in the preset order of measurement objects and judging a factor stored in the factor storage unit 12b corresponding to a measurement item as an abnormality factor when a plurality of measurement values regarding the measurement item (the same measurement item) have consecutively been judged to be abnormal (step S309). Then, the control unit 13 judges whether there exists a factor that has been judged as an abnormality factor of a measurement result (step S310). If the result of the judgment is affirmative, the control unit 13 notifies the operator of information on the abnormality factor through the notification unit 101 and the display unit 10 (step S311) and ends the process. If the result of the judgment in the step S310 is negative, the control unit 13 ends the process.

This analytical process is performed for each measurement item of the analysis of each sample.

When the approximation formula stored corresponding to the measurement item is selected and read out from the approximation formula storage unit 12a of the storage unit 12 in the step S301 in FIG. 3, an approximation formula corresponding to the measurement item is selected from a plurality of approximation formulas representing time-variations of the absorbance. An approximation formula most suitable for each measurement item is stored as a table in advance. An approximation formula corresponding to the measurement item is then selected by use of the table.

In the absorbance measurement process in the step S302, absorbance data of one measurement or the average of multiple measurements is input from the photometry mechanism 8 as the absorbance. The absorbance measurement process employs a measurement method where light of two types of wavelengths is used: the light of the first wavelength at which the absorbance greatly changes with the color change accompanying the reaction between the sample and the reagent (primary wavelength); and the light of the second wavelength at which the absorbance scarcely changes with the color change (secondary wavelength). The process then outputs the difference between the absorbance of the primary wavelength light and the absorbance of the secondary wavelength light as the absorbance data.

In the approximation parameter calculation in the step S304, the values of the parameters in the formula (approximation parameters) are calculated so that the difference between the time-variation of the absorbance represented by the approximation formula selected in the step S301 and the time-variation of the actual absorbance will be as small as possible. Specifically, the parameter values in the formula are determined so that the square error between the measured absorbance data and the absorbance, at the times of the absorbance measurement, calculated by use of the approximation formula will be as small as possible. While the existing least-squares method is usable for the calculation of the parameter values, parameter values minimizing the square error are calculated by means of the steepest descent method, for example, as a method capable of handling various types of formulas. In a reaction where two or more reagents are used, a great change in the absorbance starts after a reagent causing the primary absorbance change (generally, the final reagent) is added. In this case, only the data after the addition of the reagent causing the primary absorbance change is used for the calculation of the parameter values.

FIG. 4 is a schematic diagram showing an approximation parameter setting screen.

In FIG. 4, the setting screen 400 includes a factor setting part 401 for selecting a factor (key information), a threshold setting part 402 for setting a threshold value of each approximation parameter for judging whether the factor affects the measurement accuracy or not, a cancel button 404 for canceling the settings, and an enter (OK) button 403 for storing and enabling the settings. The approximation parameters is set by operation of the setting screen 400 displayed on the display unit 10 by use of the input unit 11. Specifically, setting the key information by use of the factor setting buttons 401 and inputting each numerical value in the threshold setting part 402 are included in the operation.

FIG. 5 is a schematic diagram showing the rough design of a data reference screen for setting display conditions of the measurement results on a measurement result display screen.

In FIG. 5, the data reference screen 500 includes a condition setting part 501 for selecting a method for sorting the data (measurement results), a condition setting part 502 for selecting an item to be displayed, a selection setting part 503 for selecting an analysis device to be displayed, a selection setting part 504 for setting the number of pieces of data to be displayed in one column (COLUMN DISPLAY NUMBER), and a start button 505 for starting a process of extracting data in accordance with the currently set conditions and displaying the extracted data on the display unit 10. The conditions that can be set in the sorting condition setting part 501 include "in order of sample ID", "in order of cell number", "in order of analysis measurement time", and "in order of analyses in each analysis item". FIG. 5 shows a case where "in order of sample ID" has been selected as the sample sorting condition, the first analysis device has been selected as the object of the displaying, and the number of pieces of data to be displayed in one column has been set at 33.

FIGS. 6-9 are schematic diagrams showing an example of a measurement result display screen which is displayed on the display unit 10 when the start of the display is commanded on the setting screen shown in FIG. 5.

FIG. 6 is a schematic diagram showing a case where a sample unit has been judged as an abnormality factor.

In FIG. 6, the measurement result display screen 600 includes a sample ID display part 601, an analysis item display part 602 and a judgment result display part 603 regarding the abnormality judgment.

The judgment result display part 603 displays images representing the temporal change of the measurement value of each analysis item in the reaction process in regard to each sample ID. Each judgment result is displayed while changing its display status depending on the status of the judgment. For example, a display example 604 is displayed when the judgment result is "data outside a reference value range", a display example 605 is displayed when the judgment result is "reference data", a display example 606 is displayed when the judgment result is "abnormal judgment data", a display example 607 is displayed when the judgment result is "device alarm", and a display example 608 is displayed when the judgment result is "abnormal judgment and device alarm".

FIG. 7 is a schematic diagram showing a case where the reagent pipetter has been judged as an abnormality factor.

In FIG. 7, the measurement result display screen 700 shows an example of display in a case where "in order of cell number" has been selected as the sorting condition, the first analysis device has been selected as the object of the displaying, and the number of pieces of data to be displayed in one column has been set at 20 on the data reference screen 500 shown in FIG. 5. The measurement result display screen 700 includes a cell number display part 701 and a judgment result display part 702.

The judgment result display part 702 displays images representing the temporal change of the measurement value of each reaction cell in the reaction process. Similarly to the case of the measurement result display screen 600 (see FIG. 6), each judgment result is displayed while changing its display status depending on the status of the judgment.

FIG. 8 is a schematic diagram showing a case where a reaction cell unit has been judged as an abnormality factor.

In FIG. 8, the measurement result display screen 800 shows an example of display in a case where "in order of analysis measurement time" has been selected as the sorting condition, the first analysis device has been selected as the object of the displaying, and the number of pieces of data to be displayed in one column has been set at 20 on the data reference screen 500 shown in FIG. 5. The measurement result display screen 800 includes an analysis measurement time display part 801 and a judgment result display part 802.

The judgment result display part 802 displays images representing the temporal change of the measurement value of each reaction cell in the reaction process. Similarly to the case of the measurement result display screen 600 (see FIG. 6), each judgment result is displayed while changing its display status depending on the status of the judgment.

Figures 9, 10:
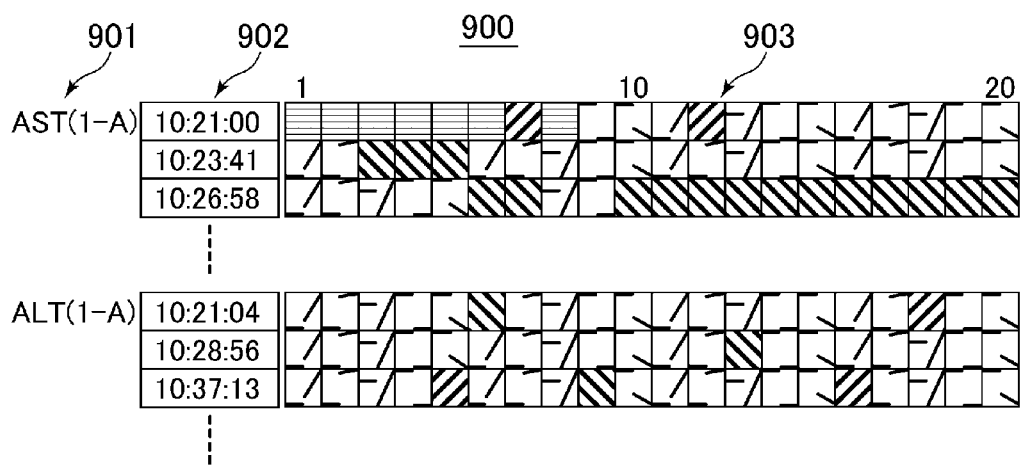
FIG. 9 is a schematic diagram showing an example of a measurement result display screen which is displayed on the display unit when a reagent bottle unit has been judged as an abnormality factor.
FIG. 10 is a schematic diagram showing an example of a measurement result display screen which is displayed on the display unit (an example of a judgment result display screen in a factor judgment process).

FIG. 9 is a schematic diagram showing a case where a reagent bottle unit has been judged as an abnormality factor.

In FIG. 9, the measurement result display screen 900 shows an example of display in a case where "in order of analysis items" has been selected as the sorting condition, the first analysis device has been selected as the object of the displaying, and the number of pieces of data to be displayed in one column has been set at 20 on the data reference screen 500 shown in FIG. 5. The measurement result display screen 900 includes an analysis item name display part 901, a measurement time display part 902 and a judgment result display part 903.

The judgment result display part 903 displays images representing the temporal change of the measurement value of each reaction cell in the reaction process. Similarly to the case of the measurement result display screen 600 (see FIG. 6), each judgment result is displayed while changing its display status depending on the status of the judgment.

FIG. 10 is a schematic diagram showing an example of a judgment result display screen in the factor judgment process.

In FIG. 10, the judgment result display screen 200 includes a key information display part 201, a score display part 202 and an analysis result comment display part 203. In the judgment results displayed on the measurement result display screen 900 shown in FIG. 9, the status of the reaction process of a reagent AST measured in a unit 1-A is displayed in chronological order. Since the judgment results from the tenth column of the line of 10:26-58 are displayed in the display status of "abnormal judgment data", it can be judged that an abnormality due to a reagent AST in the unit 1-A has occurred. Specifically, in the factor judgment process, the judgment results of the abnormality judgment process are referred to in order of the reaction cells as the preset order of measurement objects. Since a plurality of measurement values have consecutively been judged to be abnormal in regard to the same measurement time, the reagent AST in the unit 1-A as the factor stored in the factor storage unit 12*b* corresponding to the measurement item is judged as an abnormality factor.

The operation of the present embodiment configured as above will be described below.

The measurement accuracy of an automatic analysis device is determined by a combination of a plurality of performance control factors such as the dispensation quantity (dispensation accuracy) of the sample or the reagent to the reaction cell and the uniformity/stability of the reagent or the standard solution. Thus, in a case where an abnormality has occurred in a measurement result, it would be necessary to eliminate the abnormality in the measurement result and reduce the deterioration in the measurement accuracy by determining the factor causing the abnormality (causative factor) and improving the status of the factor. However, the aforementioned conventional technology has no description in regard to the determination of the causative factor even though the automatic analysis device according to the conventional technology is capable judging the occurrence of an abnormality in the measurement result. Particularly, in a case where an abnormality has occurred in an automatic analysis device for clinical examination, it would be extremely hard for the operator to quickly determine the causative factor in regard to a large number of samples to be analyzed and improve the situation. The conventional technology has plenty of room for improvement in this regard.

In contrast, the data processing device according to the present embodiment and the automatic analysis device using the data processing device are configured to include: an approximation formula storage unit which stores an approximation formula of time-variation of a measurement value regarding each of measurement items and parameters specifying the approximation formula in regard to each measurement item; a factor storage unit which stores each factor previously specified as a factor that could affect measurement accuracy of each of the measurement items, while associating each factor with each measurement item; an abnormality judgment unit which judges the presence/absence of an abnormality in the measurement value of each measurement item on the basis of the approximation formula and the parameters of the approximation formula; a factor judgment unit which refers to the results of the judgment by the abnormality judgment unit in a preset order of measurement objects, and would judge as an abnormality factor a factor stored in the factor storage unit in association with a measurement item in a case where a plurality of measurement values regarding the measurement item have consecutively been judged to be abnormal; and a notification unit which notifies an operator of the abnormality factor on the basis of the result of the judgment by the factor judgment unit. With this configuration, the deterioration in the measurement accuracy can be reduced through the detection of an abnormality in the measurement result and the determination of the causative factor. Further, it will be possible to investigate the cause of abnormality in the device by use of daily inspection data of a greater number of inspection items than ever. This contributes to the maintaining of high performance of the device and the improvement of the operation rate of the device.

DESCRIPTION OF REFERENCE CHARACTERS 1 sample disk
2 reagent disk
3 reaction disk
4 reaction bath
5 sample pipetter
6 reagent pipetter
7 stirring mechanism
8 photometry mechanism
9 cleaning mechanism
10 display unit
11 input unit
12 storage unit
13 control unit
14 piezoelectric element driver
15 stirring mechanism controller
16 sample bottle
17, 19 circular disk
18 reagent bottle
20 cooling unit
21 reaction cell
22 reaction cell holder
23 drive mechanism
24, 27 probe
25, 28 support shaft
26, 29 arm
33 nozzle
34 vertical drive mechanism
101 notification unit
102 analysis compartment
103 judgment unit

The invention claimed is:
1. An automatic analysis device comprising:
a sample pipetter which dispenses one or more samples to be measured into a plurality of reaction cells, the sample being stored in a sample bottle;
a reagent pipetter which dispenses one or more reagents stored in one or more reagent bottles into the reaction cells;
a measurement unit which measures absorbance of reaction liquids of the samples and the reagents dispensed into the reaction cells in regard to a plurality of measurement items and generates a plurality of measurement values for each of the reaction liquids in the reaction cells and each of the measurement items;
a controller programmed to control the sample pipette, the reagent pipette and the measurement unit,
wherein the controller is further programmed to execute:
an approximation formula storage unit which stores one or more approximation formulas representing time-variations for each of the measurement items and a plurality of parameters specified for the approximation formulas in regard to each of the measurement items;
a factor storage unit which stores a plurality of predetermined factors that affect measurement accuracy of the measurement values of each of the measurement items, and each of the factors being associated with the measurement items;
an abnormality judgment unit which judges whether one or more abnormalities are respectively present in the measurement values of each of the reaction liquids on the basis of the approximation formulas and the parameters thereof;
a factor judgment unit which, when the abnormalities are judged to be present, refers to the abnormalities in a preset order of sample dispensation by the sample pipetter, and judges an abnormality factor from among the factors stored in the factor storage unit when the measurement values regarding different ones of the measurement items have consecutively been judged to be abnormal in the preset order; and a notification unit which outputs a notification of the abnormality factor.

2. An automatic analysis device comprising:
a sample pipetter which dispenses one or more samples to be measured into a plurality of reaction cells, the sample being stored in a sample bottle;
a reagent pipetter which dispenses one or more reagents stored in one or more reagent bottles into the reaction cells;
a measurement unit which measures absorbance of reaction liquids of the samples and the reagents dispensed into the reaction cells in regard to a plurality of measurement items and generates a plurality of measurement values for each of the reaction liquids in the reaction cells and each of the measurement items;
a controller programmed to control the sample pipette, the reagent pipette and the measurement unit,
wherein the controller is further programmed to execute:
an approximation formula storage unit which stores one or more approximation formulas representing time-variations for each of the measurement items and a plurality of parameters specified for the approximation formulas in regard to each of the measurement items;
a factor storage unit which stores a plurality of predetermined factors that affect measurement accuracy of the measurement values of each of the measurement items, and each of the factors being associated with the measurement items;
an abnormality judgment unit which judges whether one or more abnormalities are respectively present in the measurement values of each of the reaction liquids on the basis of the approximation formulas and the parameters thereof;
a factor judgment unit which, when the abnormalities are judged to be present, refers to the abnormalities in a preset order of use of the reaction cells, and judges an abnormality factor from among the factors stored in the factor storage unit when the measurement values regarding different ones of the measurement items have consecutively been judged to be abnormal in the preset order; and
a notification unit which outputs a notification of the abnormality factor.

3. An automatic analysis device comprising:
a sample pipetter which dispenses one or more samples to be measured into a plurality of reaction cells, the sample being stored in a sample bottle;
a reagent pipetter which dispenses one or more reagents stored in one or more reagent bottles into the reaction cells;
a measurement unit which measures absorbance of reaction liquids of the samples and the reagents dispensed into the reaction cells in regard to a plurality of measurement items and generates a plurality of measurement values for each of the reaction liquids in the reaction cells and each of the measurement items;
a controller programmed to control the sample pipette, the reagent pipette and the measurement unit,
wherein the controller is further programmed to execute:
an approximation formula storage unit which stores one or more approximation formulas representing time-variations for each of the measurement items and a plurality of parameters specified for the approximation formulas in regard to each of the measurement items;
a factor storage unit which stores a plurality of predetermined factors that affect measurement accuracy of the measurement values of each of the measurement items, and each of the factors being associated with the measurement items;
an abnormality judgment unit which judges whether one or more abnormalities are respectively present in the measurement values of each of the reaction liquids on the basis of the approximation formulas and the parameters thereof;
a factor judgment unit which, when the abnormalities are judged to be present, refers to the abnormalities in a preset order of reagent dispensation by the reagent pipetter, and judges an abnormality factor from among the factors stored in the factor storage unit when the measurement values regarding different ones of the measurement items have consecutively been judged to be abnormal in the preset order; and
a notification unit which outputs a notification of the abnormality factor.

* * * * *